US00PP23308P3

(12) United States Plant Patent
Egger

(10) Patent No.: US PP23,308 P3
(45) Date of Patent: Jan. 1, 2013

(54) ***HEUCHERA* PLANT NAMED 'VIENNA'**

(50) Latin Name: ***Heuchera* spp.**
Varietal Denomination: Vienna

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 127 days.

(21) Appl. No.: 13/066,124

(22) Filed: Apr. 6, 2011

(65) Prior Publication Data

US 2012/0260381 P1 Oct. 11, 2012

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu

(74) *Attorney, Agent, or Firm* — Klarquist Sparkman, LLP

(57) ABSTRACT

A new and distinct cultivar of *Heuchera* plant characterized by multicolored leaves with a heavy silver white veil, narrow wands of pink flowers, reblooming, and excellent tolerance to heat and humidity.

1 Drawing Sheet

Botanical denomination: *Heuchera* spp.
Variety designation: 'Vienna'.

BACKGROUND OF THE INVENTION

The present invention relates to a new and distinct cultivar of *Heuchera* hybrid and given the cultivar name of 'Vienna'. *Heuchera* is in the family Saxifragaceae. *Heuchera* 'Vienna' originated from a planned breeding cross between *Heuchera* 1021-1, a proprietary unreleased plant, as the seed parent, and *Heuchera* 1021-5, a proprietary unreleased plant, as the pollen parent. Compared to the seed parent the new cultivar has foliage colored rose red to khaki rather than yellow. Compared to the pollen parent the new cultivar has a pink rather than a white flower.

This new *Heuchera* is uniquely distinguished by:

1. multicolored leaves with a heavy silver white veil,
2. narrow wands of pink flowers,
3. reblooming,
4. excellent tolerance to heat and humidity.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a one-year-old plant of *Heuchera* 'Vienna' growing in a one gallon container in greenhouse in June in Canby, Oreg.

FIG. 2 shows a one-year-old grown in the trial field in full sun in September in Canby, Oreg.

DETAILED PLANT DESCRIPTION

The following is a detailed description of the new *Heuchera* cultivar based on observations taken in September of a one-year-old specimen grown in a one gallon container in a shade house in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5th edition.

Plant:

- *Form*.—Basal rosette, herbaceous perennial.
- *Hardiness*.—USDA Zone 4 to 9.
- *Size*.—13 cm tall from top of the foliage to the ground and 36 cm wide.
- *Habit*.—Mounding.
- *Crown number*.—7.
- *Vigor*.—Good.
- *Roots*.—Fibrous, freely branching, fine, and white in color; roots develop easily from cuttings.

Leaf:

- *Type*.—Simple.
- *Arrangement*.—Rosette.
- *Shape*.—Broadly ovate.
- *Lobing/division*.—5 to 9 shallow lobes.
- *Venation*.—Palmate.
- *Margins*.—Crenate.
- *Apex*.—Mucronulate.
- *Base*.—Cordate.
- *Blade size*.—Grows to 13 cm long and 12 cm wide.
- *Surface texture*.—Glandular on both sides.
- *Petiole description*.—Grows to 12 cm long and 3 mm wide, glandular hairs, Greyed Purple 187C.
- *Leaf color*.—Variable depending amount of light, temperature, and age of the leaf; new growth topside Greyed Red 178A on veins and margins but covered over with a veil of silver white, closest to Black 202D, giving a blended color; bottom side Red Purple 59A; mature leaves topside lighten to Grey Brown N199B with veil Greyed Green 198A; older leaves are Green N137A with veil Greyed Green 198A, bottomside Red Purple 59A.

Inflorescence:

*Size*.—Grows to 18 cm long and 7 cm wide.

*Type*.—Thyrse.

*Number of flowers per thyrse*.—About 100 per thyrse.

*Number of thyrse*.—About 10 in first bloom.

*Peduncle*.—Grows to 36 cm tall, 4 mm wide at base, Greyed Purple 187A, glandular hairs, with no stem leaves.

*Pedicel*.—Variable in size, with glandular hairs, Greyed Purple 187A.

*Bloom period*.—July to October in Canby, Oreg.

Flower bud:

*Size*.—3 mm wide and 6 mm long.

*Description*.—Glandular puberulent, ovoid.

*Color*.—Red 55C on top ⅔ and Red 55A on bottom ⅓.

Flower:

*Type*.—Perfect.

*Shape*.—Campanulate.

*Size*.—6 mm long and 6 mm wide.

*Petal description*.—5 in number, 3 mm long and 1 mm wide, reflexed, spatulate, tip obtuse, base attenuate, margin entire to irregular, sparsely glandular on both sides; Red 55D with Red 55B on tip.

*Calyx description*.—Campanulate, 6 mm long and 6 mm wide, with 5 lobes, divided ⅔ way to the base, each 3 mm long and 2.7 mm wide, glandular hairs on both sides, tip obtuse, margin entire, outside color Red Purple 58A on bottom to Red 55B to Red 55D on lobes to Red 53A on lobe tips, inside Red 55D with tips Red 53A.

*Stamen description*.—5 in number, filaments 2 mm long, White N155B, anthers 0.5 mm, Red Orange 32C, pollen none, male sterile.

*Pistil description*.—1, 2-beaked, 4 mm long, ovary 2 mm long and Yellow White158B, style 2 mm long and White NN155B.

*Fragrance*.—None.

*Lastingness*.—Each thyrse blooms for about 2 weeks on the plant.

Fruit and seed: None produced.

Pest and disease tolerance: Excellent disease resistance to powdery mildew, the common problem of *Heuchera*. Susceptible to *Heuchera* rust and root weevils.

I claim:

1. A new and distinct cultivar of *Heuchera* plant as herein illustrated and described.

* * * * *

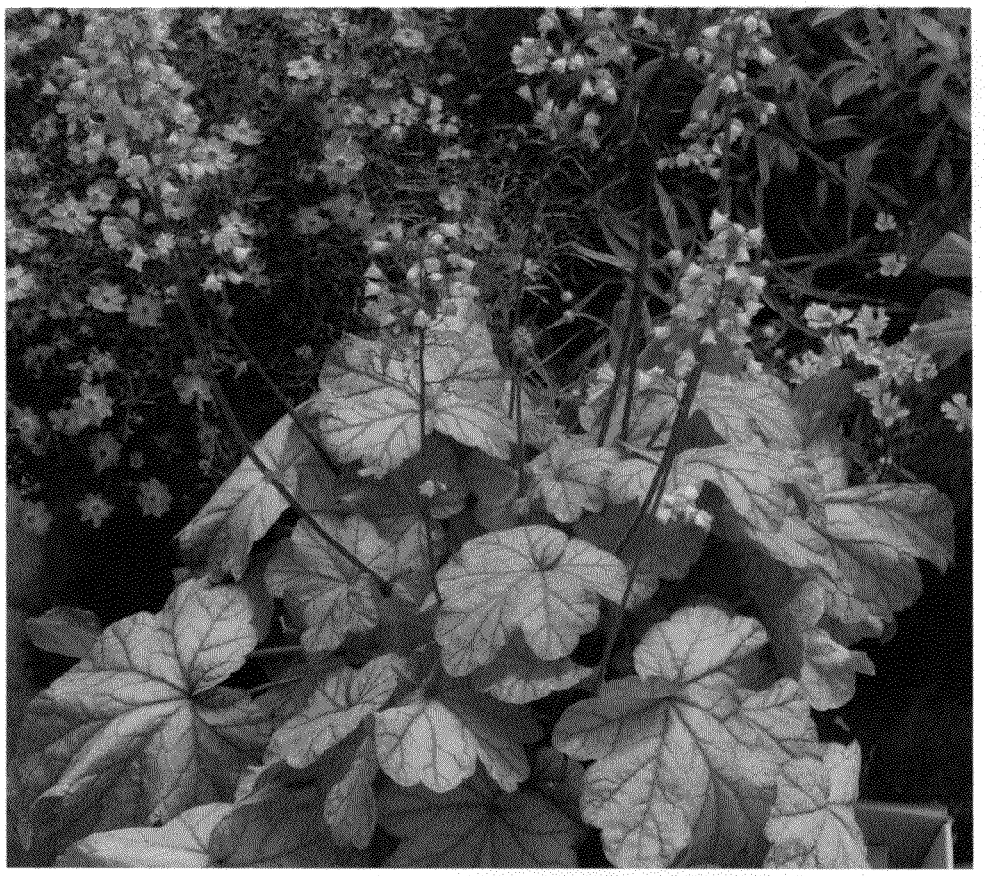
Figure 1 above,
Figure 2 to right
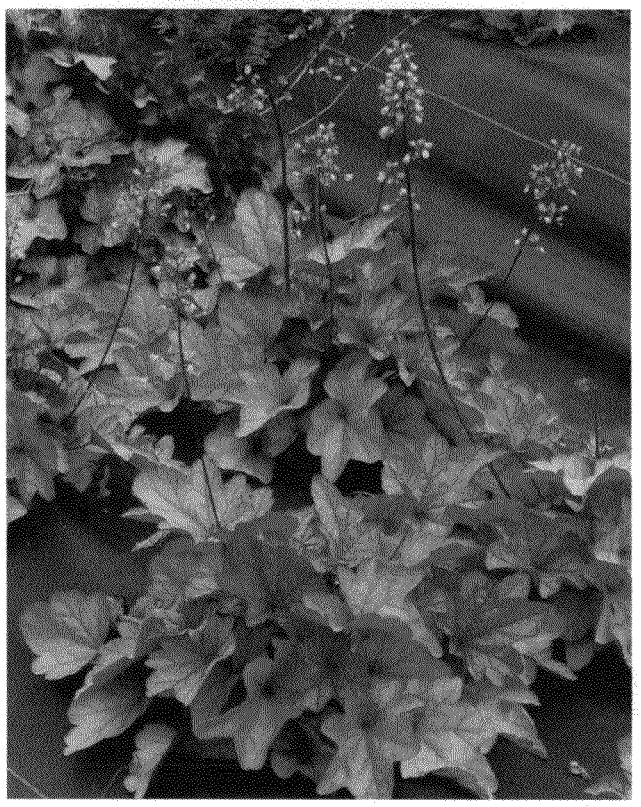

UNITED STATES PATENT AND TRADEMARK OFFICE

CERTIFICATE OF CORRECTION

PATENT NO. : PP23,308 P3
APPLICATION NO. : 13/066124
DATED : January 1, 2013
INVENTOR(S) : Janet N. Egger It is certified that error appears in the above-identified patent and that said Letters Patent is hereby corrected as shown below:

In the Specification:

Column 1, line 16, the following paragraph should be added:

--Compared to *Heuchera* 'Pinot Gris' (US Plant Patent No. 19,592) and *Heuchera* 'Encore' (US Plant Patent No. 19,578), the new cultivar has foliage that is more intensely colored and very showy reblooming pink flowers and tight inflorescences rather than light pink flowers and more open inflorescences.--.

Signed and Sealed this
Seventeenth Day of September, 2013

Teresa Stanek Rea
*Deputy Director of the United States Patent and Trademark Office*